United States Patent
Ebel et al.

(10) Patent No.: US 6,222,059 B1
(45) Date of Patent: Apr. 24, 2001

(54) PROCESS FOR THE MANUFACTURE OF ALIPHATIC ALPHA, OMEGA AMINO NITRILES

(75) Inventors: Klaus Ebel, Lampertheim; Rolf Fischer, Heidelberg; Klemens Flick, Herxheim; Martin Merger, Frankenthel; Guido Voit, Schriesheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,570

(22) PCT Filed: Sep. 1, 1997

(86) PCT No.: PCT/EP97/04733

§ 371 Date: Mar. 10, 1999

§ 102(e) Date: Mar. 10, 1999

(87) PCT Pub. No.: WO98/11059

PCT Pub. Date: Mar. 19, 1998

(30) Foreign Application Priority Data

Sep. 10, 1996 (DE) ................................ 196 36 767
Nov. 11, 1997 (DE) ................................ 196 46 436

(51) Int. Cl.$^7$ ..................... C07C 255/04; C07C 209/22; B01J 20/34
(52) U.S. Cl. ........................... 558/459; 558/452; 502/31; 502/74; 502/103; 502/177; 502/252; 502/245; 564/492; 564/511
(58) Field of Search ..................................... 558/459, 452; 502/31, 252, 245, 74, 103, 177; 564/492, 511

(56) References Cited

U.S. PATENT DOCUMENTS

| 3,696,153 | 10/1972 | Kershaw et al. . |
| 5,527,946 | 6/1996 | Flick et al. . |

FOREIGN PATENT DOCUMENTS

| 42 35 466 | 4/1994 | (DE) . |
| 44 46 893 | 7/1996 | (DE) . |
| 93/16034 | 8/1993 | (WO) . |
| 96/18603 | 6/1996 | (WO) . |

Primary Examiner—Floyd D. Higel
Assistant Examiner—Ebenezer Sackey
(74) Attorney, Agent, or Firm—Keil & Weinkauf

(57) ABSTRACT

A process for preparing aliphatic alpha,omega-amino nitrites by partial hydrogenation of aliphatic alpha,omega-dinitriles in the presence of a catalyst, wherein the catalyst used for the partial hydrogenation comprises (a) iron or a compound based on iron or mixtures thereof and (b) from 0.01 to 5% by weight, based on (a), of a promoter based on 2,3,4 or 5 elements selected from the group consisting of aluminum, silicon, zirconium, titanium and vanadium and (c) from 0 to 5% by weight, based on (a), of a compound based on an alkali metal or alkaline earth metal.

13 Claims, No Drawings

PROCESS FOR THE MANUFACTURE OF ALIPHATIC ALPHA, OMEGA AMINO NITRILES

This application is a 371 of PCT/EP 97/04733 filed Sep. 01, 1997.

The present invention relates to a process for Preparing aliphatic alpha,omega-amino nitrites in the presence of a catalyst.

DE-A 44 468 93 discloses a process for preparing aliphatic alpha,omega-amino nitrites by partial hydrogenation of aliphatic alpha,omega-dinitriles at elevated temperature and elevated pressure in the presence of a solvent and of a catalyst by using a catalyst which comprises (a) a compound based on a metal selected from the group consisting of nickel, cobalt, iron, ruthenium and rhodium, and (b) from 0.01 to 25, preferably from 0.1 to 5, % by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and (c) from 0 to 5, preferably from 0.1 to 3, % by weight, based on (a), of a compound based on an alkali metal or an alkaline earth metal, with the proviso that component (a) does not consist on the basis of iron or iron and one of the metals selected from the group consisting of cobalt, ruthenium and rhodium when (b) is a promoter based on a metal selected from the group consisting of titanium, manganese, chromium and molybdenum, and with the further proviso that when a compound based on only ruthenium or rhodium or ruthenium and rhodium or nickel and rhodium is chosen as component (a), the promoter (b) can be omitted if required.

The disadvantage of this process is the formation of by-products which can be separated only with great difficulty from the alpha,omega-amino nitrites, such as 6-aminocapronitrile or, where appropriate, other required products, such as adiponitrile and hexamethylenediamine in the case of 6-aminocapronitrile as alpha,omega-amino nitrile.

Thus, for example in the case of the hydrogenation of adiponitrile to 6-aminocapronitrile and hexamethylenediamine, there is formation in varying amounts of, inter alia, 1-amino-2-cyanocyclopentene (ICCP), 2-aminomethyl.cyclopentylamine (AMCPA), 1,2-diaminocyclohexane (DCH) and bishexamethylenetriamine (BHMTA). U.S. Pat. No. 3,696,153 discloses that AMCPA and DCH can be separated from hexamethylenediamine only with great difficulty.

Furthermore, the useful life of the catalysts in this process is not entirely satisfactory.

It is an object of the present invention to provide a process for preparing aliphatic alpha,omega-amino nitrites by partial hydrogenation of aliphatic alpha,omega-dinitriles in the presence of a catalyst which does not have said disadvantages and which allows alpha,omega-amino nitriles to be prepared with high selectivity in an industrially straightforward and economic manner.

We have found that this object is achieved by a process for preparing aliphatic alpha,omega-amino nitriles by partial hydrogenation of aliphatic alpha,omega-dinitriles in the presence of a catalyst, wherein the catalyst used for the partial hydrogenation comprises (a) iron or a compound based on iron or mixtures; thereof and (b) from 0.01 to 5% by weight, based on (a), of a promoter based on 2,3,4 or 5 elements selected from the group consisting of aluminum, silicon, zirconium, titanium and vanadium and (c) from 0 to 5% by weight, based on (a), of a compound based on an alkali metal or alkaline earth metal.

Preferred catalyst precursors are those in which component (a) contains from 90 to 100% by weight, 95 to 100% by weight [sic, preferably 92 to 99% by weight, 96 to 99% by weight [sic], and in particular 98 to 99% by weight, based on (a), of iron oxides, iron hydroxides, iron oxyhydroxides or mixtures thereof. Suitable examples thereof are iron(III) oxide, iron(II,III) oxide, iron(II) oxide, iron(II) hydroxide, iron(III) hydroxide or iron oxyhydroxide such as FeOOH. It is possible to use synthetic or natural iron oxides, iron hydroxides or iron oxyhydroxides such as magnetic iron ore (magnetite), which in the ideal case can be described by $Fe_3O_4$, brown iron ore, which in the ideal case can be described by $Fe_2O_3.H_2O$ or red iron ore (hematite), which in the ideal case can be described by $Fe_2O_3$.

Further preferred catalyst precursors are those in which component (b) contains from 0.01 to 5% by weight, preferably 0.5 to 4% by weight, in particular 1 to 3% by weight, of a promoter based on 2,3,4 or 5 elements selected from the group consisting of aluminum, zirconium, silicon, titanium and vanadium, such as aluminum, silicon and vanadium.

Further preferred catalyst precursors are those in which component (c) contains from 0 to 5% by weight, 0 to 0.5% by weight [sic], preferably 0.05 to 0.4% by weight, 0.1 to 3% by weight [sic], in particular 0.1 to 0.2% by weight, of a compound based on an alkali metal or alkaline earth metal, preferably selected from the group consisting of lithium, sodium, potassium, rubidium, cesium, magnesium and calcium.

The catalysts according to the invention can be unsupported or supported catalysts. Examples of suitable carrier materials are porous oxides such as alumina, silica, aluminosilicates, lanthanum oxide, titanium dioxide, zircon dioxide, magnesium oxide, zinc oxide and zeolites, and active carbon or mixtures thereof.

Preparation as a rule takes place by precipitating precursors of component (a) if required together with precursors of the promoter components (b) and, if required, with precursors of the trace components (c) in the presence or absence of carrier materials (depending on which type of catalyst is required), if required processing the resulting catalyst precursor to extrudates or tablets, drying and subsequently calcining. Supported catalysts can in general also be obtained by impregnating the carrier with a solution of components (a), (b) and, if required, (c), it being possible to add the individual components simultaneously or successively, or by spraying components (a), if required (b) and (c), onto the carrier by conventional methods.

Suitable precursors of components (a) are, as a rule, iron salts which are readily soluble in water, such as nitrates, chlorides, acetates, formates and sulfates, preferably nitrates.

Suitable precursors of components (b) are, as a rule, salts or complex salts, which are readily soluble in water, of the abovementioned metals and metalloids, such as nitrates, chlorides, acetates, formates and sulfates, preferably nitrates.

Suitable precursors of components (c) are, as a rule, salts, which are readily soluble in water, of the abovementioned alkali metals and alkaline earth metals, such as hydroxides, carbonates, nitrates, chlorides, acetates, formates and sulfates, preferably hydroxides and carbonates.

The precipitation generally takes place from aqueous solutions, as selected by adding precipitants, by altering the pH or by changing the temperaure.

The resulting catalyst intermediate is normally dried at from 80 to 150, preferably from 80 to 120, ° C.

The calcination is normally carried out at from 150 to 500, preferably from 200 to 450,° C. in a stream of air or nitrogen.

The catalyst composition resulting after the calcination is generally exposed to a reducing atmosphere (activation), for example by exposing it to a hydrogen atmosphere or a gas mixture containing hydrogen and an inert gas such as nitrogen, at from 200 to 500, preferably from 250 to 400, ° C. for 2 to 24 h. The catalyst loading in this case is preferably 200 l per 1 of catalyst.

The catalyst is advantageously activated directly in the synthesis reactor because this normally makes an intermediate step which is otherwise necessary, namely passivation of the surface, normally at from 20 to 80, preferably from 25 to 35, ° C. using oxygen/nitrogen mixtures such as air, unnecessary. The activation of passivated catalysts is then preferably carried out in the synthesis reactor at from 180 to 500, preferably from 200 to 350,° C. in a hydrogen-containing atmosphere.

The catalysts can be employed as fixed bed catalysts in upflow or downflow procedures or as suspended catalysts.

The starting materials employed in the process according to the invention are aliphatic alpha,omega-dinitriles of the formula I

NC—(CH$_2$)$_n$—CN  I where n is an integer from 1 to 10, in particular 2, 3, 4, 5 and 6. Particularly preferred compounds I are succinonitrile, glutaronitrile, adiponitrile, pimelonitrile and suberonitrile, very particularly preferably adiponitrile.

In the process according to the invention, the dinitriles I described above are partially hydrogenated preferably in the presence of a solvent using a catalyst to alpha,omega-amino nitrites of the formula II

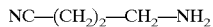

NC—(CH$_2$)$_2$—CH$_2$—NH$_2$  II where n has the abovementioned meaning. Particularly preferred amino nitrites II are those where n is 2, 3, 4, 5 or 6, in particular 4, i.e. 4-aminobutanonitrile, 5-aminopentanonitrile, 6-aminohexanonitrile (6-aminocapronitrile), 7-aminoheptanonitrile and 8-aminooctanonitrile, very particularly preferably 6-aminocapronitrile.

The temperatures chosen for carrying out the reaction in a suspension are normally in the range from 40 to 150, preferably from 50 to 100, particularly preferably from 60 to 90, ° C.; the pressure is generally chosen in the range from 2 to 30, preferably from 3 to 30, particularly preferably from 4 to 9, MPa. The residence times depend essentially on the required yield, selectivity and the required conversion; the residence time is normally selected so that a maximum yield is obtained, for example in the range from 50 to 275, preferably from 70 to 200 min.

The solvents preferably employed in the suspension procedure are ammonia, amines, diamines and triamines having 1 to 6 carbon atoms, such as trimethylamine, triethylamine, tripropylamine and tributylamine, or alcohols, in particular methanol and ethanol, particularly preferably ammonia. The dinitrile concentration is expediently chosen in the range from 10 to 90, preferably from 30 to 80, particularly preferably from 40 to 70, % of the total weight of dinitrile and solvent.

The amount of catalyst is generally selected to be in the range from 1 to 50, preferably from 5 to 20, % of the weight of dinitrile.

The suspension hydrogenation can be carried out batchwise or, preferably, continuously, as a rule in the liquid phase.

The partial hydrogenation can also be carried out batchwise or continuously in a fixed bed reactor with a downflow or upflow procedure, in which case the temperature is normally chosen in the range from 20 to 150, preferably from 30 to 90, ° C. with a pressure in the range, as a rule, from 2 to 40, preferably from 3 to 30, MPa. The partial hydrogenation is preferably carried out in the presence of a solvent, preferably ammonia, amines, diamines and triamines having 1 to 6 carbon atoms, such as trimethylamine, triethylamine, tripropylamine and tributylamine, or alcohol, preferably methanol and ethanol, particularly preferably ammonia. In a preferred embodiment, the ammonia content is chosen in the range from 1 to 10, preferably from 2 to 6, g per g of adiponitrile. Moreover, the space velocity is preferably chosen in the range from 0.1 to 2.0, preferably from 0.3 to 1.0, kg of adiponitrile/l*h. In this case too it is possible by changing the residence time to adjust the conversion, and thus the selectivity, as required.

The partial hydrogenation can be carried out in a conventional reactor suitable for this purpose (R1 in the drawing [sic]).

The hydrogenation results in a mixture which contains 6-aminocapronitrile, hexamethylenediamine and adiponitrile.

Removal of 6-aminocapronitrile, hexamethylenediamine and a portion which essentially contains adiponitrile from the mixture can take place in a conventional way, preferably by distillation, for example, as disclosed in DE-A195 002 22 or German Application 19 548 289.1, simultaneously or successively.

The distillation in the first column K1 in the drawing [sic]) is carried out by carrying out [sic] the mixture essentially comprising 6-aminocapronitrile, hexamethylenediamine, ammonia, adiponitrile and hexamethyleneimine, preferably a mixture essentially comprising from 1 to 70, preferably from 5 to 40, % by weight of 6-aminocapronitrile, from 1 to 70, preferably from 5 to 40, % by weight of adiponitrile, from 0.1 to 70, preferably from 1 to 40, % by weight of hexamethylenediamine, from 0.01 to 10, preferably from 0.05 to 5, % by weight of hexamethyleneimine and from 5 to 95, preferably from 20 to 85, % by weight of ammonia, as a rule in a conventional distillation column at a bottom temperature in the range from 60 to 250, preferably from 100 to 200, ° C. under a pressure in the range from 5 to 30, preferably from 12 to 25, bar in the presence of one or more compounds A which are inert under the distillation conditions and which boil in the range 45 from 60 to 220° C. under 18 bar, to result in ammonia as distillate and a bottom product I, with the ammonia not being completely removed.

Suitable as compound A are substances which are inert under the distillation conditions and have a boiling point in the range from 60 to 250, preferably from 60 to 150, ° C. under 18 bar. Examples which may be mentioned are:

alkanes, cycloalkanes, aromatic compounds, naphthenes, alcohols, ethers,, nitrites and amines with the abovementioned properties, in particular $C_5$-C8-alkanes and $C_2$-$C_4$-alkanols, particularly preferably n-pentane, cyclohexane, triethylamine, ethanol, acetonitrile, n-hexane, di-n-propyl ether, isopropanol, n-butylamine, benzene, very particularly preferably ethanol.

The amount of compound A added is normally in the range from 0.1 to 50, preferably from 1 to 10, % of the weight of the bottom product I.

The bottom product I, essentially comprising 6-aminocapronitrile, hexamethylenediamine, adiponitrile, hexamethyleneimine, inert compound(s) A and ammonia, the ammonia content being lower than the discharge from reactor R1, is subjected to a second distillation to result in a mixture of inert compound(s) A and ammonia as distillate and a bottom product II, the distillation being carried out at a bottom temperature in the range from 100 to 250, preferably from 140 to 200, ° C. under a pressure in the range from 2 to 15, preferably from 4 to 12 bar, with the proviso that the pressures in the first and the second column (K2 in the drawing [sic]) are coordinated so that with a bottom temperature not exceeding 250° C. in each case the distillate temperature is above 20° C. It may also be advantageous to carry out the condensation of the distillate from the second column at lower temperatures, in which case the distillate, which consists of pure or highly concentrated ammonia, is returned to the first column, or the distillate from the second column is returned, after the pressure has been increased by a compressor, as vapor to the first column or the condenser thereof.

The bottom product II, essentially comprising 6-aminocapronitrile, hexamethylenediamine, adiponitrile, hexamethyleneimine and inert compound(s) A is subjected to distillation in a third column (K3 in the drawing [sic]) to result in the inert compound(s) A as distillate and a bottom product III, the distillation being carried out at a bottom temperature in the range from 50 to 250, preferably from 140 to 200, ° C. under a pressure in the range from 0.05 to 2, preferably from 0.2 to 1, bar, with the proviso that the inert compound(s) A resulting as distillate are fed into the second column and, if required, the distillation is carried out in the presence of one or more compound(s) B which are inert under the distillation conditions and which boil in the range from 20 to 250, preferably from 60 to 170,° C. under 0.3 bar.

Examples which may be mentioned of compound B are:

alkanes, cycloalkanes, aromatic compounds, naphthenes, alcohols, ethers, nitrites and amines with the abovementioned properties, in particular di-n-butyl ether, valeronitrile, n-octane, cyclo-octane, n-hexylamine, hexamethyleneimine, hexamethylenediamine, preferably hexamethyleneimine and/or hexamethylenediamine, particularly preferably hexamethyleneimine.

In a preferred embodiment, hexamethyleneimine and/or hexamethylenediamine is chosen as compound B or, particularly preferably, no further compound B is added.

Compound B is preferably fed into column K3 in an amount in the range from 0.01 to 50, preferably from 0.5 to 10, % of the weight of bottom product II.

Bottom product III, essentially comprising 6-aminocapronitrile, hexamethylenediamine, adiponitrile, hexamethyleneimine and, if required, inert compound(s) B, is subjected to a distillation in a fourth column (K4 in the drawing [sic]) to result in a distillate KP1 essentially comprising hexamethyleneimine, if required inert compound(s) B and a sidestream product SA1 essentially comprising hexamethylenediamine, with the bottom temperature of the column being in the range from 50 to 250° C. and the pressure being in the range from 0.05 to 1.5 bar to result in a bottom product IV.

If required, the column is equipped with a partition in the region between the feed and the sidestream (Petlyuk column) so that the hexamethylenediamine obtained is essentially free of hexamethyleneimine and inert compound (s) B, and from other low boilers, where the distillate KP1 and/or HMD from the sidestream product SA1 is, if required, fed to the third column or, where appropriate, only partly fed to the third column and the remainder is discharged.

The bottom product IV, essentially comprising 6-aminocapronitrile and adiponitrile, and any high boilers, is subjected in a fifth column (K5 in the drawing [sic]) to a distillation to result in 6-aminocapronitrile with a purity of at least 95%, preferably 99 to 99.9%, as distillate and a sidestream product V, consisting essentially of adiponitrile, and a bottom product V, which consists of high boilers and small amounts of adiponitrile.

If required, the column is equipped with a partition in the region between feed and sidestream so that the adiponitrile obtained has lower contents of high boilers, the distillation being carried out at a bottom temperature in the range from 50 to 250° C. under a pressure in the range from 10 to 300 mbar.

It is also possible, instead of obtaining adiponitrile as sidestream product V, to fractionate the bottom product V from column K5, comprising adiponitrile and higher-boiling compounds, by distillation in another column K6, to result in adiponitrile as distillate VI.

The part which essentially comprises adiponitrile and results from the described workup by distillation of the reaction mixture resulting from the hydrogenation of adiponitrile as sidestream product V from column k5 [sic], as distillate VI from column K6 or as bottom product from column D5 [sic], preferably as sidestream product V from column D5 [sic], is treated according to the invention with an acid or an acidic ion exchanger.

Substances primarily suitable as acids or acidic ion exchangers are those able to act as proton donors to primary, secondary and tertiary saturated and unsaturated amines such as enamines. Particularly suitable for this purpose are acids with a $P_{Ka}$ [sic] not exceeding 10, preferably not exceeding 7.

Acids which can be employed are inorganic acids such as nitric acid, preferably sulfuric acid, in particular as 100% by weight sulfuric acid or as a mixture containing at least 90% by weight, preferably 96% by weight, in particular with water or phosphoric acid, organic acids, for example carboxylic acids such as adipic acid, 2-ethylhexanoic acid, pimelic acid, suberic acid, undecanedioic acid, terephthalic acid, cyclohexanecarboxylic acid, for example sulfonic acid [sic] such as p-toluenesulfonic acid, benzenesulfonic acid, and examples of acidic ion exchangers which can be employed are Lewatit S100G1, Amberlyst 15, Dowex 50 WX 8, Bay. Kat. K 2431, Amberlite IR-120 and mixtures of such acids and acidic ion exchangers.

The reaction of adiponitrile with the acid can take place in the presence of a liquid diluent such as water, it being possible to add the liquid diluent together with the acid before or after the addition of acid to the adiponitrile.

Direct treatment of the adiponitrile still mixed with higher-boiling compounds, for example the bottom product V from column K5, if the latter contains no adiponitrile sidestream, is likewise possible. In this case there is an increase in the amount of acid or acidic ion exchanger used and in the amount of residue resulting after removal of adiponitrile.

The molar ratio of the acid groups to the basic compounds present in the residue should be at least equimolar, preferably above equimolar. It has proven advantageous to add from 0.01 to 10% by weight, in particular 0.1 to 2% by weight, of acid based on adiponitrile.

The reaction of adiponitrile with the acid can take place in a conventional way, such as by mixing or by passing the adiponitrile over a fixed bed of ion exchanger, advantageously at from 2 to 250° C., in particular 30 to 100° C., which results in reaction times of from 1 second to 30 minutes, in particular 1 second to 10 minutes.

Adiponitrile can be removed from the mixture in a conventional way, advantageously by distillation or extraction.

If a liquid diluent such as water is added in the reaction of the residue with the acid, the liquid diluent can be removed, before removal of the adiponitrile, preferably by adsorption, in particular by distillation.

It is likewise possible and advantageous for the reaction products obtained after the addition of acid and, where appropriate, excess acid to be removed from the adiponitrile by extraction, for example with water.

The adiponitrile obtained by the process according to the invention can be used anew for the partial hydrogenation to hexamethylenediamine and 6-aminocapronitrile, avoiding an increase in the level of by-products which prevent the preparation of hexamethylenediamine and/or 6-aminocapronitrile complying with specifications and/or have an adverse effect on the useful life of the catalyst for the partial hydrogenation.

The process according to the invention results in alpha, omega-amino nitrites in good selectivities and with smaller amounts of by-products than in the prior art. Furthermore, the catalysts employed according to the invention have a distinctly longer useful life than comparable catalysts from the prior art. The alpha,omega-amino nitrites are important starting materials for preparing cyclic lactams, in particular 6-aminocapronitrile for caprolactam.

The meanings in the examples are:
ADN=adiponitrile
ACN=6-aminocapronitrile
HMD=hexamethylenediamine
DCH=cis+trans-1,2-diaminocyclohexane
AMCPA=1-amino-2-aminomethylcyclopentane
BHMTA=bis-hexamethylenetriamine
ICCP=1amino-2-cyanocyclopentene

Example 1 a) Preparation of Catalyst

A mixture of magnetite, potassium carbonate, $Al_2O_3$, and calcium carbonate was heat-treated, and the solidified melt was crushed and screened as described by A. B. Stiles, T. A. Koch, Catalyst Manufacture (1995), pages 167/68, to result in the following oxide composition: 1.1% by weight of $K_2O$, 3.0% by weight of $Al_2O_3$, 2.3% by weight of CaO, 0.11% by weight of Si, 0.01% by weight of Ti, remainder Fe oxides.

This composition was subsequently reduced in an $N_2/H_2$ stream at 450° C. for 72 h, passivated at room temperature with an $N_2$/air mixture (24 h with 1% air in nitrogen), the temperature in the catalyst bed not exceeding 45° C., and washed with water for 7 days.

The resulting catalyst had the following composition: 1.2% by weight of Al, 0.74% by weight of Ca, 0.02% by weight of K, 0.11% by weight of Si, 0.01% by weight of Ti, remainder Fe/Fe oxide. The total of group b) promoters is 1.32% by weight, and the total of group c) promoters, calculated as oxides, is 1.06% by weight.

b) Partial hydrogenation of ADN to ACN

A tubular reactor (length 180 cm, d=30 mm) was packed with 740 ml (1819 g) of the catalyst composition prepared as in (a) and reduced under atmospheric pressure in a stream of hydrogen (500 l(STP)/h). This entailed the temperature being raised from 30° C. to 340° C. over the course of 24 h and then kept at 340° C. for 72 h. After the temperature had been reduced, a mixture of 400 ml/h ADN, 1140 ml/h $NH_3$ and 500 l(STP)/h $H_2$ was fed into the reactor under 250 bar. After running at 110° C. for 9700 h, the ADN conversion was 45%, the ACN selectivity was 42% and the HMD selectivity was 57%. Also found were 3700 ppm DCH, 55 ppm AMCPA, 30 ppm ICCP and 1560 ppm BHMTA.

Example 2 a) Preparation of Catalyst

The catalyst was prepared by heating a magnetite ore at 15000° C. under nitrogen for 6 hours. The magnetite ore had the following composition: 72% by weight of Fe, 0.07% by weight of Al, 0.03% by weight of Ca, 0.04% by weight of Mg, 0.11% by weight of Si, 0.01% by weight of Ti, remainder oxygen. The total of group b) promoters is 0.19% by weight, and the total of group c) promoters, calculated as oxides, is 1.03% by weight.

The cooled block of melt was comminuted in a jaw crusher, and a particle size fraction from 1.5 to 3 mm was screened out. The oxide catalyst was reduced in an $H_2/N_2$ stream at 4500° C. for 72 hours. After cooling to room temperature under nitrogen, the Fe catalyst was passivated with an $N_2$/air stream (24 h with 1% air in nitrogen), taking care that the temperature in the catalyst bed did not exceed 45° C.

b) Partial Hydrogenation of ADN to ACN

Three tubular reactors connected in series (total length 4.5 m, d=6 mm) were packed with 141 ml (239 g) of the catalyst prepared in Example 1a) (1.5–3 mm chips) and then reduced under atmospheric pressure in a stream of hydrogen (200 l/h). For this purpose, the temperature was raised from 70° C. to 340° C. over the course of 24 hours and then kept at 340° C. for 72 hours. After the temperature had been reduced, a mixture of 75.0 ml/h ADN, 365 ml/h NH3 [sic] and 200 l(STP)/h H2 [sic] was fed into the reactor under 250 bar. The test was carried out for 950 hours. No decrease in catalyst activity or ACN yield and selectivity was observed. The results obtained under the stated conditions as a function of the temperature were as follows (Table 1):

TABLE 1

| Temperature [° C.] | ADN Conversion [%] | ACN Selectivity [%] | HMD Selectivity [%] | ACN + HMD Selectivity [%] | DCH | AMCPA [ppm, based on HMD] | BHMTA | ICCP |
|---|---|---|---|---|---|---|---|---|
| 80 | 47.3 | 80.4 | 18.5 | 98.9 | 3700 | 430 | | 80 |
| 90 | 72.1 | 67.3 | 31.7 | 99.0 | 2900 | 250 | | 48 |
| 96 | 89.4 | 48.8 | 50.2 | 99.0 | 2100 | 120 | 990 | 60 |
| 107 | 99.9 | 0.6 | 98.6 | 99.2 | 1200 | 25 | | 53 |

The results in Tab. 1 show that the ACN/HMD ratio can be set as required in the presence of the catalysts according to the invention, and that ACN+HMD selectivities of about 99% are achieved. They further demonstrate that the amount of DCH and AMCPA based on hexamethylenediamine depends on the ADN conversion. Less DCH and AMCPA (based on HMD) is present as more HMD is produced.

U.S. Pat. No. 4,282,381, Column 2, Table 1, discloses the average amounts of by-products resulting in the hydrogenation of adiponitrile to hexamethylenediamine in the presence of iron catalysts. These are 2400–4000 ppm for DCH, 100–300 ppm for AMCPA and 3000–5000 ppm for BHMTA.

It was not to be foreseen and was thus surprising that smaller, not larger, amounts of DCH and AMCPA and BHMTA are formed when ACN/HMD mixtures are prepared in the presence of the iron catalysts according to the invention (see, for example, Tab. 1, ACN selectivity 48.8%).

Example 3 a) Preparation of Catalyst

The catalyst was prepared by heating (at 1500° C. under nitrogen for 6 hours) a mixture of a magnetite ore which was intimately mixed with 3.4% by weight $Al_2O_3$. The magnetite ore had the following composition: 72% by weight Fe, 0.07% by weight Al, 0.03% by weight Ca, 0.04% by weight Mg, 0.11% by weight Si, 0.01% by weight Ti, remainder oxygen.

The cooled block of melt was comminuted in a jaw crusher, and a particle size fraction from 1.5 to 3 mm was screened out. Analysis of the catalyst precursor obtained in this way showed the following composition: 69.6% by weight Fe, 1.81% by weight Al, 0.029% by weight Ca, 0.038% by weight Mg, 0.11% by weight Si, 0.01% by weight Ti, remainder oxygen. The total of group b) promoters is 1.93% by weight, and the total of group c) promoters, calculated as oxides, is 1.04% by weight.

The oxide catalyst was reduced in an $H_2/N_2$ stream at 450° C. for 72 hours. After cooling to room temperature under nitrogen, the Fe catalyst was passivated with an $N_2$/air stream (24 h with 1% air in nitrogen), taking care that the temperature in the catalyst bed did not exceed 45° C.

b) Partial Hydrogenation of ADN to ACN

The adiponitrile hydrogenation was carried out with the iron catalyst described in Example 3a). The conditions for catalyst activation and the amounts of ADN, ammonia and hydrogen fed in per hour corresponded to Example 2b).

Table 2 contains the ADN conversion and ACN and HMD selectivities, and the amounts of subsidiary components, obtained on hydrogenation at 97° C.

TABLE 2

| Temperature [° C.] | ADN Conversion [%] | ACN Selectivity [%] | HMD Selectivity [%] | ACN + HMD Selectivity [%] | ACH | AMCPA [ppm, based on HMD] | BHMTA | ICCP |
|---|---|---|---|---|---|---|---|---|
| 97 | 91.8 | 46.4 | 52.9 | 99.3 | 1900 | 90 | 900 | 55 |

We claim:

1. A process for preparing aliphatic alpha,omega-amino nitriles by partial hydrogenation of aliphatic alpha,omega-dinitriles in the presence of a catalyst, wherein the catalyst used for the partial hydrogenation comprises (a) iron or a compound based on iron or mixtures thereof and (b) from 0.01 to 5% by weight, based on (a), of a promoter based on 2,3,4 or 5 elements selected from the group consisting of aluminum, silicon, zirconium, titanium and vanadium and (c) from 0 to 5% by weight, based on (a), of a compound based on an alkali metal or alkaline earth metal.

2. A process as claimed in claim 1, wherein an iron oxide or mixtures of iron oxides is employed as compound based on iron.

3. A process as claimed in claim 1, wherein a promoter based on aluminum, silicon and vanadium is employed.

4. A process as claimed in claim 1, wherein the catalyst is a supported catalyst.

5. A process as claimed in claim 1, wherein the catalyst is an unsupported catalyst.

6. A process as claimed in claims 1, wherein adipo-nitrile is employed as dinitrile, and 6-aminocapronitrile is obtained.

7. A process as claimed in claim 1 for the simultaneous preparation of 6-aminocapronitrile and hexamethylene-diamine starting from adiponitrile by (1) partial hydrogenation of adiponitrile in the presence of a catalyst to obtain a mixture comprising 6-aminocapronitrile, hexamethylenediamine and adiponitrile and (2) removal of 6-aminocapronitrile and hexamethylene-diamine from the mixture.

8. A process as claimed in claim 7, wherein from 0.01 to 10% by weight of an acid or an acidic ion exchanger, based on adipo-nitrile, are added to the remaining part which essentially comprises adiponitrile, and the adiponitrile is removed from the mixture.

9. A process as claimed in claim 7 wherein the adiponitrile is removed from the mixture by distillation, and an acid whose boiling point is above the boiling point of adiponitrile under the pressure chosen for the distillation is employed.

10. A process as claimed in any of claim 7, wherein an acid with a $pK_a$ not exceeding 10 is employed.

11. A process as claimed in claim 7, wherein the adiponitrile obtained after the process is employed anew for the simultaneous preparation of 6-aminocapronitrile and hexamethylenediamine starting from adiponitrile.

12. A process as claimed in claim 1, wherein the hydrogenation is carried out in a suspension.

13. A process as claimed in claim 1, wherein the hydrogenation is carried out in a fixed bed reactor.

* * * * *

UNITED STATES PATENT AND TRADEMARK OFFICE
CERTIFICATE OF CORRECTION

PATENT NO. : 6,222,059 B1
DATED : April 24, 2001
INVENTOR(S) : Ebel et al.

It is certified that error appears in the above-identified patent and that said Letters Patent is hereby corrected as shown below:

Abstract,
Line 1, "nitrites" should be -- nitriles --.

Signed and Sealed this

Sixth Day of November, 2001

Attest:

NICHOLAS P. GODICI
Attesting Officer — Acting Director of the United States Patent and Trademark Office

UNITED STATES PATENT AND TRADEMARK OFFICE
CERTIFICATE OF CORRECTION

PATENT NO. : 6,222,059 B1
DATED : April 24, 2001
INVENTOR(S) : Ebel et al.

Page 1 of 1

It is certified that error appears in the above-identified patent and that said Letters Patent is hereby corrected as shown below:

<u>Title page,</u>
Item [30], "Nov. 11, 1997" should be -- Nov. 11, 1996 --.

Signed and Sealed this

Twenty-sixth Day of November, 2002

Attest:

Attesting Officer

JAMES E. ROGAN
*Director of the United States Patent and Trademark Office*